United States Patent [19]

Moore

[11] Patent Number: 4,820,990

[45] Date of Patent: Apr. 11, 1989

[54] ELECTRODE-LESS DETECTOR

[75] Inventor: Zack Moore, Lake Jackson, Tex.

[73] Assignee: Zeta Management Ltd., Lake Jackson, Tex.

[21] Appl. No.: 107,290

[22] Filed: Oct. 9, 1987

[51] Int. Cl.4 .............................................. G01R 5/28
[52] U.S. Cl. .................................. 324/445; 324/453;
73/864.16; 73/864.35
[58] Field of Search ........... 73/863.83, 863.84, 864.21,
73/864.34, 864.35, 864.16; 324/453, 445, 458,
453, 61 P, 65 P; 128/734

[56] References Cited

U.S. PATENT DOCUMENTS

| | | |
|---|---|---|
| 2,297,640 | 9/1942 | Webb . |
| 3,368,145 | 2/1968 | Gerdes . |
| 4,220,921 | 9/1980 | Hach ................................. 324/450 |
| 4,297,640 | 10/1981 | Moore . |
| 4,446,435 | 5/1984 | Canzoneri . |
| 4,449,101 | 5/1984 | Canzoneri et al. . |

FOREIGN PATENT DOCUMENTS

| | | | |
|---|---|---|---|
| 229928 | 11/1985 | Fed. Rep. of Germany ...... | 128/734 |
| 831692 | 3/1960 | United Kingdom ................ | 324/445 |
| 894264 | 4/1962 | United Kingdom ................ | 324/445 |

Primary Examiner—Reinhard J. Eisenzopf
Assistant Examiner—Jose M. Solis
Attorney, Agent, or Firm—Steele, Gould & Fried

[57] ABSTRACT

An electrodeless apparatus for determining a function of the electrical charge condition in a flowable liquid media containing electrical charge influencing species comprising a tubular flow path member, the flow path member having electrically insulating walls, an open end and a closed end, the flow path being so disposed that it may be substantially filled with the liquid, a reciprocating member whose outer wall is electrically insulating disposed within the flow path member, the reciprocating member having a transverse cross-sectional configuration such that the reciprocating member fits adjacent but spaced from the electrically insulating walls of the flow path member, an annulus for admitting predetermined amounts of flowable material to the flow path member, a sensor disposed on the non-wetted side of the flow path member for developing a signal proportional to a desired ion activity by electrostatic or inductive coupling, and means coupled to said sensor for amplifying any electrical signal induced across said sensor.

11 Claims, 2 Drawing Sheets

ELECTRODE-LESS DETECTOR

FIELD OF THE INVENTION

The present invention relates to a means for measuring the effects of the electrical double layer phenomena in heterogeneous electrochemical equilibria.

More particularly, the invention is concerned with an electrode-free apparatus which is useful in obtaining quantitative information on the effects of the electrical double layer in a hetergeneous electrochemical system, for example the streaming potential and/or streaming current.

BACKGROUND OF THE INVENTION

The specific absorption of ions readily occurs at the interface between a non-conductive solid and an electrolyte solution. The exposed surface of any solid is covered with adsorbed ions which define the limits of the inner Helmholtz plane. The accumulative charge making up this plane may be stoichiometrically compensated by an excess of oppositely charged ions diffusely dispersed throughout the bulk of a joining liquid phase in a direction perpendicular to the exposed solid surface. Ions of the opposite charge to those surface adsorbed can approach no closer than the outer Helmholtz plane. The space charge in the region between the outer immobile Helmholtz plane and the contacting mobile electrolyte gives rise to an electrokinetic driving force (defined as zeta potential) which plays an important role in explaining the equilibrium behavior of heterogeneous liquid-liquid or liquid-solid systems in industrial and civic processes such as flocculation control, water purification, waste management, etc. The influence of this electrical double layer upon equilibrium has been recognized for many years, however, any practical application of the concept has been seriously hampered by the absence of a suitable means of measurement.

It is conventional practice in clarifying aqueous systems containing suspended particles to employ a flocculation process. Once flocculated, the suspended particles can be separated from their fluid medium by sedimentation, filtration, floatation, centrifugation or one or more of the foregoing physical separatory processes in combination. Conventionally, the flocculation process is promoted by the use of flocculating chemicals such as alum, ferric chloride or various polymeric materials such as water-soluble cationic and anionic organic polyelectrolytes. Aqueous suspensions of finely divided polymeric particles are encountered in a paper machine headbox within a paper manufacturing process operation and in many other contexts. In a typical flocculation process for flocculating aqueous suspensions of finely divided particles, a water-soluble cationic flocculating chemical is added to the solution. The finely divided particles suspended in the solution are normally negatively charged and thus, the addition of the cationic agent results in charge neutralization on the suspended particles. When the average charge is zero, or some other predetermined value, the dispersed organic and/or inorganic particles undergo flocculation, i.e., aggregation at an increased rate. Too much cationic agent, however, creates positively charged particles which can be as difficult to flocculate as are the originally negatively charged particles.

To date, however, determining how much chemical to add to the stream to be treated has been difficult, especially since the composition of such stream often varies over fairly wide ranges and time intervals of a few minutes to a few hours.

Various empirical approaches to "finding" the correct dosage of flocculant to be added to a stream have been used. For example, increasing amounts of flocculant may be added to samples from the stream and the amount of decrease in turbidity of the stream noted, the correct dosage being determined as the one which causes the greatest decrease in turbidity with the least addition of flocculant. Such a procedure is time consuming and therefore not really suitable where the composition of the treated solution varies, since the information resulting from this procedure is no longer valid or applicable to the treated solution since the composition of the treated solution will have varied by the time the data has been corrected.

Another approach is to use a so-called Zeta meter to determine zeta-related electrokinetic phenomena such as the charge condition existing in the stream. The Zeta meter is used to observe the time required for a single charge particle from the stream to pass a predetermined distance along a liquid path while under the influence of an electric field at a given temperature. This method is time consuming and requires a technician to perform the test and to interpret test results before the stream is treated with a greater, lesser, or the same amount of flocculant as had been used since the last previous Zeta meter test was made.

U.S. Pat. No. 3,368,145 to W. F. Gerdes discloses an apparatus which provides a continuous measurement of the charge density of the absorbed material taken from the process stream.

U.S. Pat. No. 2,297,640 to Z. J. Moore which is herein incorporated by reference discloses an apparatus for measuring the electric charge of non-conductive particles in a mildly conductive electrolyte which incorporates a grounded electrode in a special location with respect to two sensing electrodes. The electrode while effective does not completely eliminate all potential galvanic interferences and can provide no protection against the potentially corrosive action at high concentrations of reactive chemicals on the exposed metal sensing electrodes.

U.S. Pat. No. 4,446,435 to Canzoneri discloses an ultrasonic streaming current detector for developing on a continuous basis, an electrical signal which is a function of the charge condition existing in a stream containing charged particles.

U.S. Pat. No. 4,449,101 to Canzoneri et al relates to a jet wash apparatus for an ultrasonic streaming current detector with means for variably conveying a cleaning fluid into the detector.

SUMMARY OF THE INVENTION

In accordance with the present invention there is provided a means for obtaining a quantitative measure of electrokinetic properties in a two phase liquid-liquid or liquid-solid system wherein said means contains an electrically non-conductive inert barrier which separates the measured fluid from the measuring circuitry.

More particularly, the invention relates to an apparatus for determining a function of the electrical charge condition in a flowable liquid media containing electrical charge influencing species, particularly electrical charge influencing species which are electrically non-conductive themselves but on whose surface electrical charges collect.

The apparatus comprises a tubular flow path member or cylinder, open at one end and having electrically insulating walls. Sensory means is provided on the outside or non-wetted side of the cylinder for developing a signal proportional to a desired ion activity by electrostatic or inductive coupling. A block-like reciprocating member, with electrically insulating walls, located at least partially within the tubular flow path member to cause liquid located therein to flow to and fro in the flow path member in a repetitive manner. Such a block-like member can be a piston loosely fitted and slidably mounted in said flow path member, or it can be a piston with lands slidably mounted in said flow path member. Means coupled to said sensory means is provided form amplifying and utilizing any electrical signal induced across said sensory means. The flow path member is disposed so that a continuously different sample of the flowable liquid media can be passed in and out of the cylinder in the space between the walls of the tubular flow path member and the walls of the block-like reciprocating member past the sensory means.

The sensory means is either electrostatically or electromagnetically coupled to the mechanically displaced mobile ion space charge (solution ion cloud) through an inert, electrically non-conductive low dielectric barrier so as to be both chemically and galvanically protected from the effects of the measured fluid.

In accordance with a specific embodiment of the invention there is provided an apparatus for determining a function of the electrical charge condition in a flowable liquid media containing charge influencing species having an open end flow chamber composed of an electrically non-conductive, low dielectric, chemically inert material fitted with a solid electrically, non-conductive reciprocating member in a concentric relationship with the flow chamber. The combination of the two elements is so disposed that a flowable suspension may enter and exit at the open end of the chamber. The apparatus is provided with electrically conductive sensor means positioned externally to the fluid wetted surface of the chamber. A means for processing induced signals which are developed between the two elements is coupled to said sensor means.

It is therefore an object of the invention to provide an apparatus for measuring zeta-related electrokinetic phenomena such as a streaming current and/or a potential which does not have as a basic requirement the direct exposure of sensing electrodes to the measured fluid.

It is a further object of the invention to provide an apparatus for obtaining quantitative information on the effects of an electrical electrochemical system having a streaming potential and/or streaming current.

Other objects and a fuller understanding of the invention will be had by referring to the following description and claims of a preferred embodiment, taken in conjunction with the accompanying drawings, wherein like reference characters refer to similar parts throughout the several views.

DESCRIPTION OF THE PREFERRED EMBODIMENTS OF THE INVENTION

Figure 1:
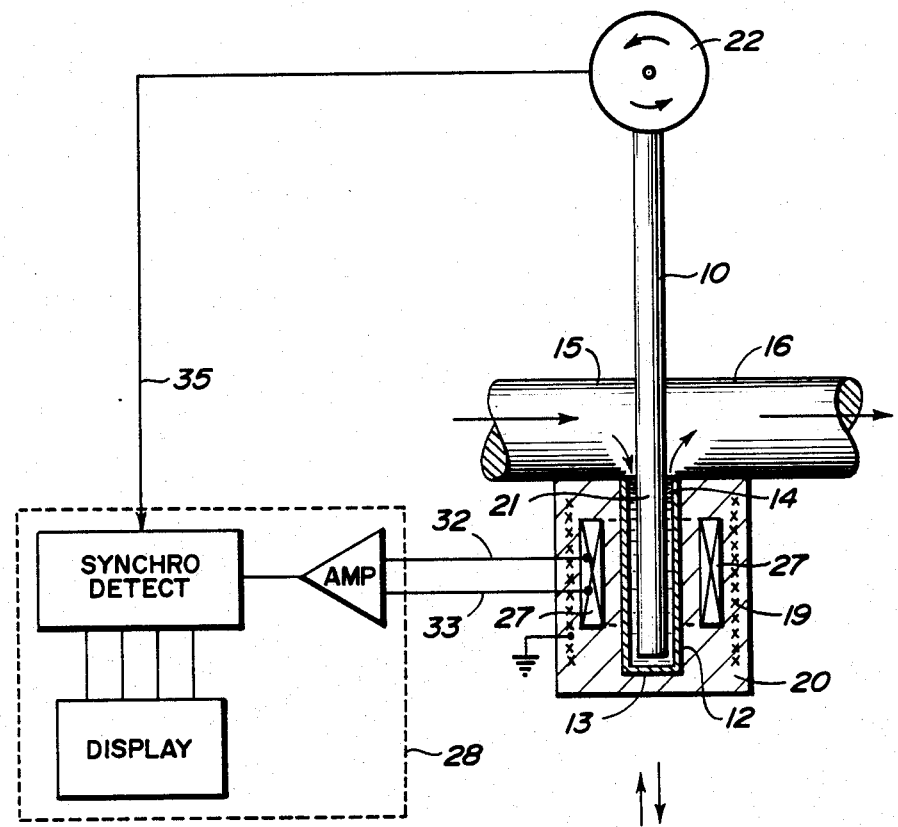
FIG. 1 is a partially diagrammatic sectional elevation of an apparatus of the invention.

Although specific terms are used in the following description for the sake of clarity, these terms are intended to refer only to the particular structure of the invention selected for illustration in the drawings, and are not intended to define or limit the scope of the invention.

Referring to the drawing, there is shown an apparatus of the type disclosed in the aforementioned U.S. Pat. No. 4,297,640, which is incorporated herein by reference, that comprises an electrically inert tubular flow path member or cylinder 12, open at its upper end and closed at the bottom end 13. The upper end 14 is open and exposed to a flowing liquid stream 15 containing a conductive electrolyte and electrical charge influencing species which are electrically non-conductive themselves but on whose surfaces electrical charges collect. A Faraday cage 19 surrounds the cylinder to minimize electrostatic interferences.

An electrically inert reciprocating member or piston 10 is located at least partially within the flow path member or cylinder 12 to cause liquid therein to flow into and out of the small open annulus 14 in a repetitive manner. The piston 10 may be loosely fitted and slidably mounted in the flow path member. If desired, the piston 10 may be provided with lands (not shown).

The piston 10 is supported and reciprocated by means of a mechanical drive package such as electric motor driven cam 22. Advantageously, the piston 10 is reciprocated at a slow frequency, for example about four cycles per second. Fluids enter the opening at the upper end on the upstroke of the piston 10 and are expelled on the down stroke. The fluids are totally contained by the piping 16 and the cylinder 12. Sensory means 27 connected to an external signal processor 28 is positioned externally to the wetted surface of the cylinder 12.

The entire cylinder 12 may be composed of galvanically non-conductive material to form a low dielectric barrier to prevent exposure with the measuring apparatus.

Figure 2:
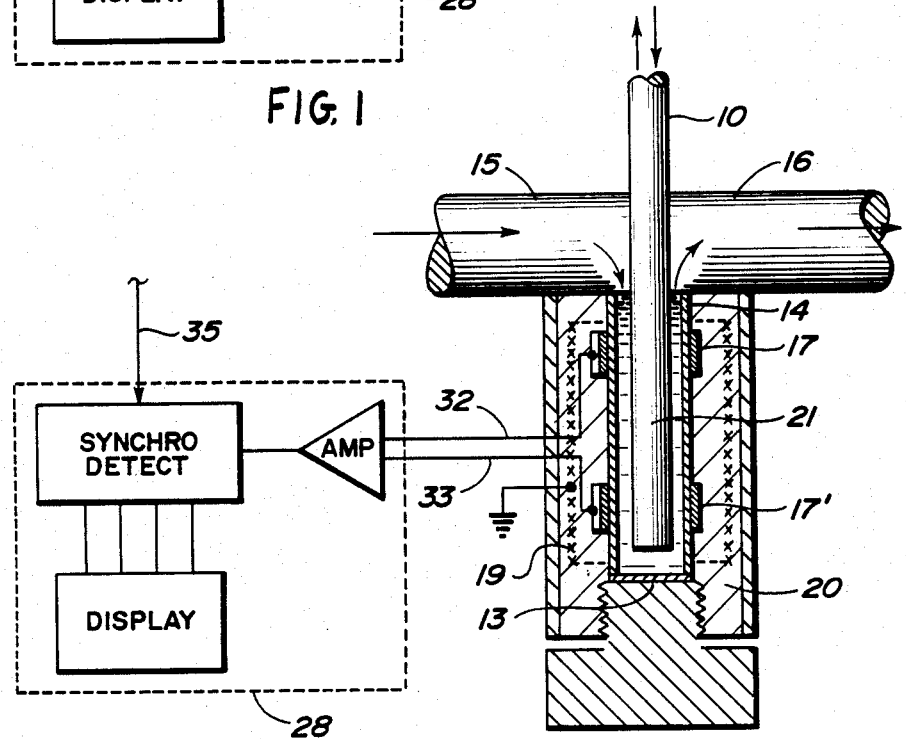
FIG. 2 is a partially diagrammatic sectional elevation of the apparatus of FIG. 1 with an electrostatic coupling.

As shown in FIG. 2, when an electrostatic coupling system is utilized, there is provided two sleeve conductors 17, 17' which are positioned on the outside or non-wetted side of the barrier cylinder 12. The conductors 17, 17' are separated from each other at a distance to provide optimum signal response based on the chosen cylinder length and piston stroke length. The conductors 17, 17' are electrically connected to signal processor 28 by lead lines 32, 33 so that electrostatically coupled signals caused to be produced in the conductors 17, 17' by the action of the reciprocating piston 10 can be simultaneously processed. A grounded Faraday cage 19 surrounds the conductors 17, 17' so as to minimize electrostatically coupled external interferences.

All of the stationary components of the measurement cell are stabilized by a low dielectric, low conductivity inert plastic support medium 20. A signal proportional to the desired ion activity in the annulus 21 is thus developed across the barrier cylinder 12.

Figure 3:
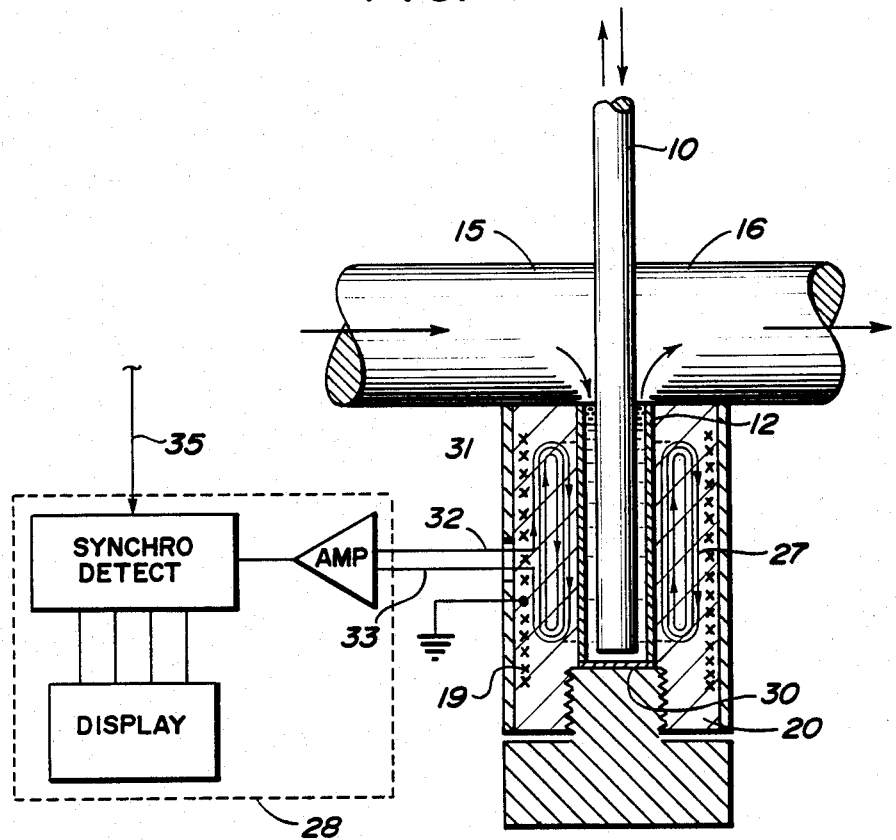
FIG. 3 is a partially diagrammatic sectional elevation of the apparatus of FIG. 1 with an inductive coupling.

As shown in FIG. 3, means are provided to develop a signal across the cylinder barrier 12 by an inductive coupling. An electromagnetic coil 22 wound in a toroidal configuration and disposed in close proximity to but separate from the process fluid by cylinder barrier 12 is inductively coupled to the ion circuit created by mechanically displaced ions in a fluid annulus 31. The electromagnetic coil 22 is electrically connected to the external signal processor 18 through electrical lead lines 32, 33 so that electromechanically induced inductively coupled signals caused to be produced by the action of the reciprocating piston 10 can be processed. A grounded Faraday cage 19 surrounds the electromagnetic coil and minimizes stray signals due to the electrostatic coupling with the external environment.

OPERATION OF THE APPARATUS

The operation of the apparatus is as follows: The medium to be monitored, generally consisting of a hetergeneous non-conducting solid suspended in an electrolyte solution 15 flow through a pipe 16, is introduced through the annulus opening 14 from a flowing stream 15. Through the reciprocating action of the piston 10, fluid flowing over the top of the cylinder 12 is drawn into the annulus 14 on the upstroke and discharged from the cell on the downstroke. With each stroke of the piston 10, a new sample is taken from the flowing stream 15. The movement of the piston 10 and the geometry of the cell annulus 21 are precisely controlled so that the pressure drop through the cell annulus is also controlled. Mechanical forces applied by the action of the piston forces the mobile liquid phase 21 (containing like counter ions) past a stationary solid phase consisting of adsorbed suspended solids of opposite charge polarity on the wetted surface of the cell walls of cylinder 12. The mobile counter ions are alternately bunched at opposite ends of the cell annulus with each stroke of the piston 10. The accumulative charge of the mechanically displaced solution ion cloud is of sufficient magnitude as to create a measurable electric force field between opposite ends of the cell. The conductors 17, 17' are located in the induced force field but separated from the fluid material by the low conductivity, low dielectric chemically inert barrier cylinder 12. An electromotive force proportional to the magnitude of the mechanically displaced accumulative charge and possessing sufficient energy as to facilitate a measurable signal, is developed between the conductors 17, 17'. One or more conductors can be located in the force field.

An alternate method of signal detection is achieved by inductive coupling through a chemically inert, galvanically non-conductive barrier as shown in FIG. 3. When mobile counter ions are physically displaced by action of the piston 10, the movement of like charges may be defined as electrical current. Ion movement so confined to the call annulus may then be compared to electron movement in an electrical conductor. Thus, inductive coupling through the inert electrically con-conductive barrier 12 to an external conductor 28 is possible. Instead of a single external conductor, a properly oriented and positioned electromagnetic coil 27 consisting of many turns is placed in close proximity to the annulus 31. Means 28 are provided to process the signals developed in the external coil resulting in a response which is proportional to the magnitude of the mobile ion charge and velocity in the cell annulus.

The streaming potential and streaming current are electrical in nature and are a function of the electrical charge on the non-conductive particles in the liquid. The streaming current and potential are proportional to this electric charge condition and alternate at the same frequency as the reciprocating frequency of the piston 10. The Faraday cage blocks stray interferences from the sensory elements.

The signal processor 28 processes the alternating current electrical signals so that they become direct current signals which are a function of the desired electrical charge conditions of the liquid.

Electronic conduction line 35 connects the mechanical package 22 to the single processor 28 so that the alternating current signals caused to be produced in lines 32, 33 by the piston 10 driven by the mechanical package 22 can be synchronously demodulated to direct current electrical signals by the signal processor 28.

Preferably the piston, barrier and/or plastic support compositions consist of any one or a combination of the following:
polyhalogenated polymers and copolymers;
polypseudohalogenated polymers and copolymers;
polyurethanes;
silica, oxides and hydroxides of silica;
silicates, nitrides, carbides, borates and borides;
metal oxides and hydrates;
resins including vinyl-ester resins;
polymeric hydrocarbons and the like.

The conductors 17, 17' may comprise any suitable electrically conductive material.

Although the invention has been described with a certain degree of particularity, it is understood that the present disclosure has been made only by way of example and that numerous changes in the details of construction and the combination and arrangement of parts may be resorted to without departing from the spirit and scope of the invention.

What is claimed is:

1. An apparatus for sensing and quantifying without the addition of an externally induced potential the electrical charge condition in a flowable two phased liquid media containing electrical charge influencing species comprising a tubular flow path member, said flow path member having electrically insulating walls, an open end and a closed end, said flow path being so disposed that it may be substantially filled with said liquid, a reciprocating member whose outer wall is electrically insulating disposed within said flow path member for mechanically inducing the ions in said liquid to flow in more than one direction, said reciprocating member having a transverse cross-sectional configuration such that said reciprocating member fits adjacent but spaced from said electrically insulating walls of said flow path member and provides a controlled pressure drop, means for admitting predetermined amounts of flowable material to said flow path member, sensory means disposed on the non-wetted side of said flow path member for solely developing a signal proportional to a desired ion activity by electrostatic or inductive coupling, and means coupled to said sensory means for amplifying any electrical signal induced across said sensory means.

2. An apparatus for sensing and quantifying electrical energy derived from zeta influenced ions in a flowable two phased liquid stream comprising:
an electrically insulated tubular flow path member having an open end and a closed end, said flow path member being disposed so as to be filled substantially with said liquid;
an electrically insulated reciprocating member disposed within said flow path, said reciprocating member having a transverse cross-sectional configuration whereby said reciprocating member fits adjacent but spaced from the walls of said flow path member, said reciprocating member causing the liquid in said flow path to flow in more than one direction and exciting ions in said liquid;

electrostatic coupling means for sensing said mechanically induced excited ions in said liquid, said coupling means being disposed on the non-wetted side of said flow path member which forms a barrier separating liquid from said coupling means, said coupling means developing a signal proportional to said mechanically induced ion activity; and, means for amplifying the electrical signals induced across said coupling means.

3. The apparatus of claim 1, wherein said sensory means develops said signal by electrostatic coupling.

4. The apparatus of claim 2, wherein said sensory means comprises at least one electrical conductor.

5. The apparatus of claim 4, wherein there is present two conductors and the combined surface area of both of said conductors is not greater than the total fluid wetted surface of said flow path member.

6. The apparatus of claim 2, wherein a Faraday cage surrounds said sensory means.

7. The apparatus of claim 1, wherein said sensory means develops said signal by inductive coupling.

8. The apparatus of claim 7, wherein said sensory means comprises an electromagnetic coil.

9. The apparatus of claim 8, including a Faraday cage surrounding said sensory means.

10. The apparatus of claim 2, including a Faraday cage surrounding said sensory means.

11. An apparatus for sensing and quantifying electrical energy derived from zeta influenced ions in a flowable two phased liquid stream comprising:

an electrically insulated tubular flow path member having an open end and a closed end, said flow path member being disposed so as to be filled substantially with said liquid;

an electrically insulated reciprocating member disposed within said flow path, said reciprocating member having a transverse cross-sectional configuration whereby said reciprocating member fits adjacent but spaced from the walls of said flow path member, said reciprocating member causing the liquid in said flow path to flow in more than one direction and exciting ions in said liquid;

inductive coupling means for sensing said mechanically induced excited ions in said liquid, said coupling means being disposed on the non-wetted side of said flow path member which forms a barrier separating liquid from said coupling means, said coupling means developing a signal proportional to said mechanically induced ion activity; and, means for amplifying the electrical signals induced across said coupling means.

* * * * *